(12) United States Patent
Heacock (10) Patent No.: US 11,890,051 B2
(45) Date of Patent: Feb. 6, 2024

(54) APPARATUS WITH FILTER TO TREAT MACULAR DEGENERATION AND METHOD OF TREATING MACULAR DEGENERATION

(71) Applicant: Sensor, LLC, Maple Valley, WA (US)

(72) Inventor: Gregory Heacock, Maple Valley, WA (US)

(73) Assignee: Sensor, LLC, Maple Valley, WA (US)

( * ) Notice: Subject to any disclaimer, the term of this patent is extended or adjusted under 35 U.S.C. 154(b) by 231 days.

(21) Appl. No.: 15/425,577

(22) Filed: Feb. 6, 2017

(65) Prior Publication Data

US 2018/0221199 A1    Aug. 9, 2018

(51) Int. Cl.
*A61B 18/20* (2006.01)
*A61F 9/008* (2006.01)
*A61B 3/12* (2006.01)
*G02C 7/04* (2006.01)

(52) U.S. Cl.
CPC ............ *A61B 18/20* (2013.01); *A61B 3/1208* (2013.01); *A61B 18/203* (2013.01); *A61B 2018/20553* (2017.05); *A61F 9/00821* (2013.01); *A61F 2009/00863* (2013.01); *G02C 7/04* (2013.01)

(58) Field of Classification Search
CPC ....... A61F 9/00821; A61F 2009/00863; A61B 2018/20553; A61B 18/203; A61B 3/10; A61B 3/12; A61B 3/13; A61B 3/1208; A61B 18/20
USPC ...................................................... 606/2–19
See application file for complete search history.

(56) References Cited

U.S. PATENT DOCUMENTS

| | | | |
|---|---|---|---|
| 4,728,183 A | 3/1988 | Heacock et al. | |
| 4,801,198 A | 1/1989 | Heacock et al. | |
| 5,007,729 A | 4/1991 | Erickson et al. | |
| 5,189,450 A | 2/1993 | Crossman et al. | |
| 5,309,187 A | 5/1994 | Crossman et al. | |
| 5,438,366 A * | 8/1995 | Jackson | G02B 5/02 348/335 |
| 5,479,221 A * | 12/1995 | Heine | A61B 3/117 351/211 |
| 5,526,189 A | 6/1996 | Heacock | |
| 5,543,816 A | 8/1996 | Heacock | |
| 5,997,141 A | 12/1999 | Heacock | |
| 6,195,016 B1 | 2/2001 | Shankle et al. | |
| 6,204,975 B1 | 3/2001 | Watters et al. | |
| 6,474,815 B1 * | 11/2002 | Ulbers | A61B 3/135 351/214 |

(Continued)

FOREIGN PATENT DOCUMENTS

EP    0293126 A1    11/1988

OTHER PUBLICATIONS

International Search Report, PCT/US18/14764, dated Jan. 23, 2018.

(Continued)

*Primary Examiner* — Pamela M. Bays
(74) *Attorney, Agent, or Firm* — McAndrews, Held & Malloy, Ltd.

(57) ABSTRACT

An apparatus is disclosed for treating macular degeneration including an optical filter configured to be mated with the ophthalmic lens, the filter having a surface wherein at least a portion of the surface comprises non-transmissive material that may distribute power from a light beam creating a plurality of light beams. A method of treating macular degeneration using the optical filter is also disclosed.

23 Claims, 6 Drawing Sheets

(56) References Cited

U.S. PATENT DOCUMENTS

| | | | |
|---|---|---|---|
| 6,851,808 B2 | 2/2005 | Heacock | |
| 7,224,822 B2 | 5/2007 | Heacock | |
| 7,248,720 B2 | 7/2007 | Muller et al. | |
| 7,288,106 B2 | 10/2007 | Heacock et al. | |
| 8,303,116 B2 | 11/2012 | Heacock | |
| 9,037,217 B1* | 5/2015 | Peyman | A61B 18/20 600/427 |
| 2006/0004306 A1 | 1/2006 | Altshuler et al. | |
| 2006/0146284 A1* | 7/2006 | Collins | A61B 3/1208 351/215 |
| 2007/0129775 A1* | 6/2007 | Mordaunt | A61F 9/008 607/88 |
| 2009/0028206 A1* | 1/2009 | Borneis | B23K 26/0604 372/102 |
| 2009/0182310 A1 | 7/2009 | Gertner et al. | |
| 2011/0071510 A1* | 3/2011 | Safraoui | A61B 18/203 606/9 |
| 2012/0314403 A1* | 12/2012 | Kennedy | F21V 9/083 362/109 |
| 2013/0317487 A1* | 11/2013 | Luttrull | A61B 18/20 606/5 |
| 2016/0270656 A1 | 9/2016 | Samec et al. | |
| 2017/0153408 A1* | 6/2017 | Clark | G02B 7/006 |

OTHER PUBLICATIONS

International Preliminary Report on Patentability, PCT/US2018/014764, dated Aug. 15, 2019.

Extended European Search Report of European Application No. 18747347.5 dated Oct. 16, 2020.

\* cited by examiner

APPARATUS WITH FILTER TO TREAT MACULAR DEGENERATION AND METHOD OF TREATING MACULAR DEGENERATION

FEDERALLY SPONSORED RESEARCH OR DEVELOPMENT

[Not Applicable]

BACKGROUND

Ophthalmic lenses are used by ophthalmologists and optometrists for diagnosis and treatment of the eye. Historically, laser energy has been used to treat eye disease by focusing the energy onto tissue and using the thermal energy of the laser to close or seal leaking blood vessels, to cauterize tissues in an effort control detachments, or in some cases to grossly kill a region of tissue or cells such as a cancerous tumor. More recently, ophthalmologists have tried, largely unsuccessfully, to use lasers to treat one retinal condition, age-related macular degeneration.

Age-related macular degeneration, also known as AMD, is a condition that may result in blurred or loss of vision in the center of the visual field. The condition is caused by deterioration of retinal cells and it is believed that the root cause of the retinal cell deterioration is related to the decrease of nutrient flow through one of the sublayers of the retina called Bruch's Membrane.

Research has shown that the reestablishment of nutrient flow through Bruch's membrane decreases the probability of a patient developing AMD. Further, studies have shown that one effective way to reestablish nutrient flow through Bruch's Membrane is to induce overlying adjacent retinal pigment epithelial cells (RPE cells) to migrate over the surface of Bruch's Membrane.

Inducing RPE cells to migrate and thus improve nutrient flow through Bruch's Membrane has been tried with existing laser therapy technology. However, the problem with existing laser energy is that the treatment (damage) area of existing laser modalities is very large compared to the size of the cells within the layers of the retinal tissue. For example, even though a typical RPE cell is about 40 microns, a typical laser has a much larger beam size with diameter of 400 to 5000 microns, resulting in damage to too many cells within a treatment area with typical laser treatments. Moreover, such large-scale destruction inhibits healthy RPE cells at the periphery of the damaged areas from appropriately migrating into the damaged areas to perform the job of improving nutrient flow, thus resulting in ineffective treatment. Some have attempted to rely on laser speckle (resulting from beam interaction with the fiber) in an attempt to mitigate the beams' damaging effects; however, such a technique has been inconsistent and unreliable.

Due to the inherent challenges of providing targeted therapy to an eye using, e.g., laser therapy, and resulting potential damage to healthy cells in the retina of the patient, an apparatus that is practical, adaptable, low-cost and safe, but can also minimize the damage to the healthy cells and tissues in the eye is needed to deliver proper treatment for a patient experiencing AMD.

Generally, this application relates to an optical filter to treat AMD and a method of treating macular degeneration using the filter. For example, this application relates to an apparatus for treating AMD that includes an optical filter that may distribute power from a light beam incident on the optical filter to a retina of the eye.

SUMMARY

The present application relates to an apparatus for treating AMD using an optical filter and a method of using the optical filter. The optical filter may be configured to selectively distribute power from light beams allowing particular cells within tissue in the eye to be targeted with therapeutic light.

In one embodiment, the apparatus for treating macular degeneration comprises an ophthalmic lens and an optical filter configured to distribute power from a light beam incident on the optical filter to the retina of the eye. In some embodiments, the ophthalmic lens is an eye contacting lens and may include a focusing lens. The focusing lens may be configured to generate a real image of the retina and the optical filter is oriented approximately coincidentally with said real image of the retina. The focusing lens may focus a plurality of light beams over a predetermined area of a retina of an eye (e.g., a portion of the retina containing diseased tissue targeted for therapy). In some embodiments, the ophthalmic lens is an aspheric lens.

The optical filter may be configured to separate and distribute power from a coherent light beam into a plurality of coherent light beams. In one embodiment, the optical filter comprises a surface with non-transmissive material that separates a light beam and a housing configured to be mated with an ophthalmic lens.

In some embodiments, one or more surfaces of the optical filter comprises a portion that includes non-transmissive material. The non-transmissive material may distribute power from a light beam into a plurality of light beams. In some embodiments, the filter may comprise a distributive element configured to selectively target cells within tissue in the eye with the distributed power from the light beams, for example, retinal pigment epithelial cells in a retina. In some embodiments, the distributive element may distribute power from the light beam and create a plurality of light beams having diameters of between about 30 and 50 microns. The filter may include, for example, a grid of non-transmissive lines on a surface of the optical filter, a grid with generally uniform lines of a non-transmissive material on a surface of the optical filter, a plurality of holes on a surface of the optical filter, a plurality of reflective squares separated by gaps including gaps of up to about 50 microns, or etched lines in a surface of the optical filter.

In some embodiments, the optical filter includes a coating with a selective reflector that reflects a narrow bandwidth of light spectra, e.g., 532 nm+/−10 nm or 532 nm+/−15 nm. For example, the selective reflector is deposited in a grid pattern and reflects particular wavelengths, dividing the therapeutic laser into a plurality of light beams while improving the image for the clinician by allowing visualization of the retinal image at all other wavelengths except the wavelength of the selective reflector. The selective reflector can reflect any appropriate wavelength and a reflector that reflects a wavelength between about 520 to 550 nm, and particularly 532 nm+/−15 nm is preferred.

In one embodiment, the non-transmissive material or distributive element of the optical filter may be configured to divide the light beam and create a plurality of light beams, allowing the plurality of light beams to create a plurality of spots on the retina having diameters of about 30 to 50 microns, preferably about 40 microns. In some embodiments, the distributed power from the light beam impinges on the retina of the eye as a plurality of light beams having a diameter of between about 30 and 50 microns measured at approximately the retinal surface. The preferred spacing between the plurality of light beams is about 30 to 50 microns, preferably about 40 microns.

In some embodiments, the input light beam directed onto the filter is a laser beam and may have a diameter between about 100 and 5000 microns and may have a wavelength between about 450 and 1064 nm. The input light beam may be applied in a series of uniform or non-uniform pulses.

In some embodiments, the optical filter is a generally transparent, planar structure orientated generally perpendicular relative to the optical axis that extends through the optical filter and the ophthalmic lens. In some embodiments, the optical filter may be angled such that spacing between parallel lines of a grid at a portion of the optical filter at a minimum distance from a source of the light beam is smaller relative to grid spacing at a maximum distance from the source based on the angle. The optical filter may be oriented approximately coincidentally with the real image of the retina.

In a preferred embodiment, the optical filter comprises a generally planar structure having first and second surfaces, wherein the first surface is designed to be closer to the ophthalmic lens than the second surface and the second surface comprises at least a portion that includes non-transmissive material or a distributive element such as a grid. In other embodiments, the first surface comprises the non-transmissive material or the distributive element.

In some embodiments, the optical filter and/or its housing may be injection molded and/or compression molded. The filter assembly may be appropriate for single use or may be reusable. The optical filter may be formed of a light transmissive substrate material such as polymethylmethacrylate with an index of refraction between about 1.35 and 1.7 and have a grid, line, or dot pattern deposited upon the substrate comprised of a blocking, reflecting or selective reflecting coating and allowing other light for visualization imaging or observation to pass around the grid, line or dot pattern. The optical filter may be integral with or separate from the ophthalmic lens. The ophthalmic lens may be a single-use or a reusable lens.

In some embodiments, the optical filter is integral with the ophthalmic lens. In another embodiment, the optical filter is configured to be mated with the ophthalmic lens such as by mounting the optical filter on an end of the ophthalmic lens or having a housing configured to be mated with an ophthalmic lens.

In one embodiment, the optical filter may have a housing that is separate from the housing of the ophthalmic lens and the optical filter may be configured such that it can be mounted on the housing of an ophthalmic lens. The optical filter can be configured as a planar element, and comprise a shape suitable for incorporation in one or both of the main body or the ring portion (e.g., a square shape, a circular shape, etc.) of the ophthalmic lens. The optical filter may also comprise a circular flange and be configured to be mounted within a housing of the ophthalmic lens.

In still another example, a method for treating macular degeneration is provided. A method for treating macular degeneration in accordance with the present application may include providing an ophthalmic lens, providing an optical filter as described herein including, for example, one configured to distribute power from a light beam incident on the optical filter to a retina of a patient's eye; mating the ophthalmic lens and filter, for example, as described herein; position the mated ophthalmic lens on or near the eye; and directing power from the light beam through the optical filter and ophthalmic lens onto the retina.

One of the advantages of the present invention is, for example, that the optical filter minimizes damage to the healthy eye tissue or cells by minimizing the power reaching the tissue and reducing the effective area of the injury site. Another advantage may be that the reduced injury site size allows healthy cells to migrate toward the treated cells further decreasing the potential injury. Another advantage is that, in one embodiment, the optical filter is designed such that it is easily mounted onto existing ophthalmic lenses and can be used with existing treatment systems reducing, for example, the need to invest in capital equipment and improving convenience for the clinician. In one embodiment, the filter is disposable or single-use limiting hazards associated with deleterious agents and controlling infection while minimizing component failures. In another embodiment, the use of a selective reflector for the coating allows improved imaging and optical quality for the clinician.

These and other objects, advantages and novel features of the present invention, as well as details of an illustrative embodiment thereof, will be more fully understood from the following description and the drawing.

The foregoing summary, as well as the following detailed description of certain embodiments of the present invention, will be better understood when read in conjunction with the appended drawings. For the purposes of illustration, certain embodiments are shown in the drawings. It should be understood, however, that the claims are not limited to the arrangements and instrumentalities shown in the attached drawings. Furthermore, the appearance shown in the drawings is one of many ornamental appearances that can be employed to achieve the stated functions of the system.

DETAILED DESCRIPTION

This invention relates to an improved method and system for treating macular degeneration by use of an optical filter that can selectively distribute power such as power from a laser onto a retina of an eye when used in conjunction with a lens such as an ophthalmic lens. In an example, the invention relates to an optical filter with a distributive or filtering pattern such as a grid or partitioning holes that can be used by a clinician in conjunction with an ophthalmic lens to deliver, e.g., laser, therapy to selected cells of the eye.

Figure 1:
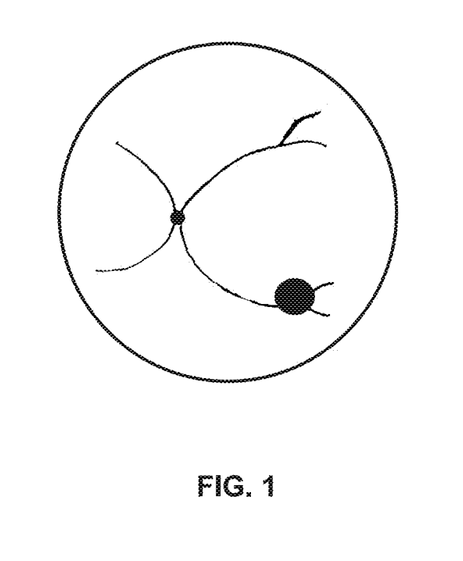
FIG. 1 depicts an illustrative representation of potential damage to a retina treated with a prior art laser beam.

As discussed above, previous attempts to treat AMD have involved, for example, using a single, powerful laser beam with a large spot size directed to a retina as shown for example in the illustration of FIG. 1. The result is that the laser produced a relatively large burn area on the retina that damages both healthy and unhealthy cells and vessels and further does not induce the healing response of RPE cell migration.

Figure 2:
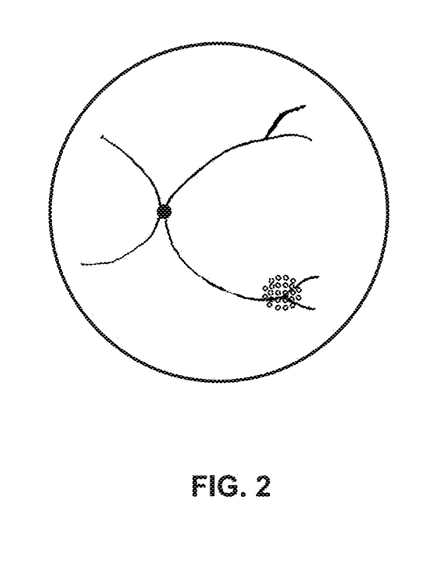
FIG. 2 depicts an illustrative representation of a retina treated with one embodiment of an optical filter as described herein.

The present application describes a filter and system that is configured to distribute power (e.g., via an optical filter) from a light source such as a laser onto a region of a diseased retina of the eye with a power and spot size that results in selective targeting of cells in a particular retinal area as shown for example in the illustration of FIG. 2. This selective targeting accordingly promotes effective migration of healthy cells into the targeted region. For example, the distributed power can selectively target and treat smaller portion of RPE cells in the retina of the eye, encouraging nearby healthy RPE cells to migrate toward the targeted, treated cells and assist in increasing nutrient flow through Bruch's membrane. In a preferred embodiment, the optical filter is designed such that individual RPE cells are treated. Thus, by damaging the targeted cells, therapy is able to mitigate the impact of macular degeneration on a diseased eye.

Figure 3:
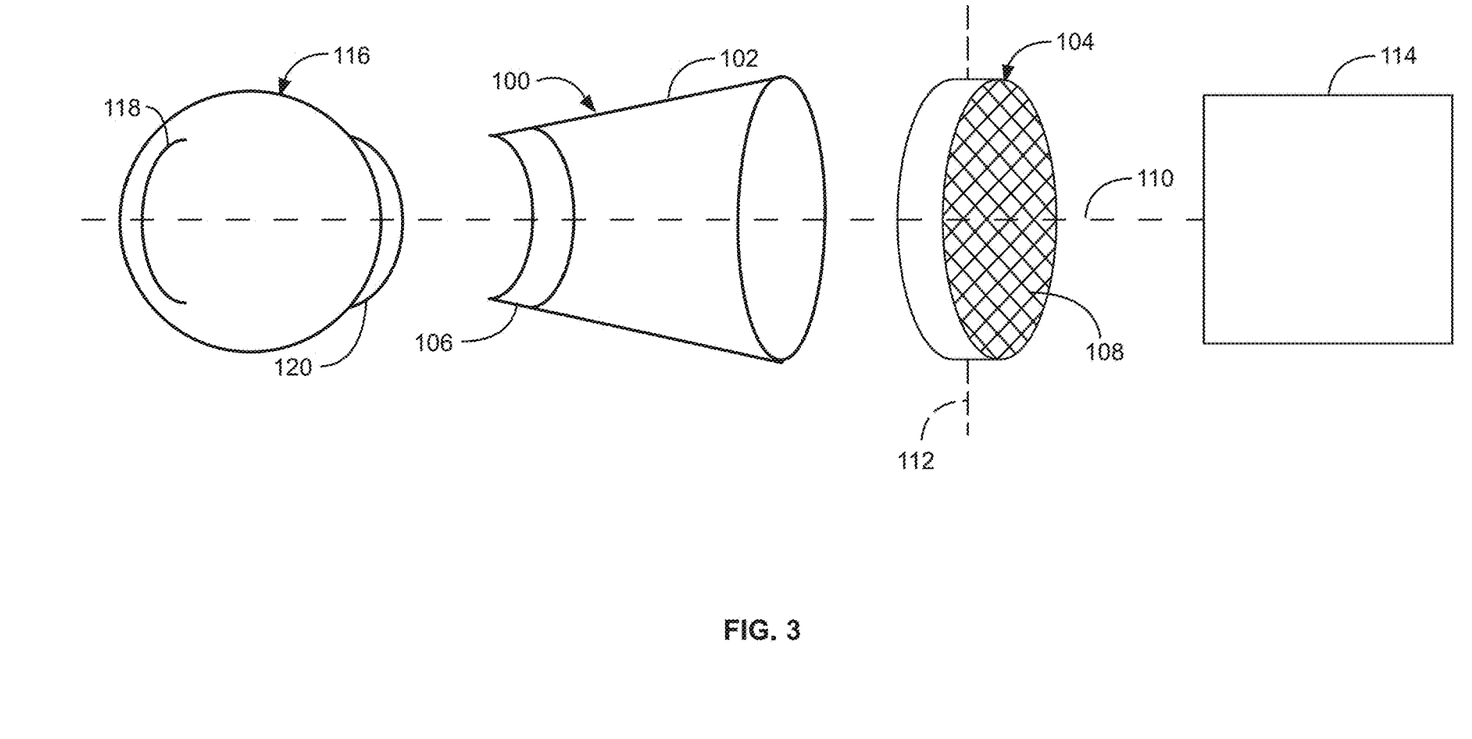
FIG. 3 depicts an eye, example apparatus with an ophthalmic lens and optical filter, and a light source.

FIG. 3 illustrates an example apparatus or system including an ophthalmic lens 100 and an optical filter 104. In the example of FIG. 3, the ophthalmic lens 100 includes a main body portion 102 that includes or that secures elements of the ophthalmic lens 100, as well as provide an easily manipulable device for a clinician. For example, the main body portion 102 can have a generally conical shape, and include one or more grip portions for easy handling. At an opposite end of the ophthalmic lens is an eye contacting portion 106 configured to closely match the curvature of a cornea 120 and which may come into contact with a patient's eye during a procedure. In the example of FIG. 3, an optical filter 104, having a filtering pattern 108, is positioned such that it can be mounted on one end of the main body portion 102 of the ophthalmic lens, preferably the end furthest from the eye contacting portion 106.

The ophthalmic lens suitable for use in the present invention may be any lens suitable for treating macular degeneration including eye contacting lenses and aspheric lenses that are known in the art. Examples of ophthalmic lenses (including disposable ophthalmic lenses including eye contacting lenses) have been disclosed, for example, in U.S. Pat. Nos. 7,281,294, 6,581,808, and 8,303,116 and U.S. patent publications 2016/0161762 and 2016/070028. Suitable eye contacting ophthalmic lenses for use with the optical filter can include, for example, 20, 28, 60, 78, and 90 Diopter lenses. The optical filter is also suitable with other ophthalmic lenses such as indirect image retina lenses, handheld aspheric lenses, and BIOM lenses.

The ophthalmic lens may be a glass lens or may be injection molded and/or compression molded to provide a single use lens and/or a reusable lens. Components of the ophthalmic lens 100 can be formed as an integrated unit (e.g., having a fixed arrangement), as individually separable, or as a combination of fixed and removable components. For example, individual features (e.g., the main body, the eye contacting portion, the focusing lens optical filter, etc.) can be formed using molding techniques and/or secured by various methods (e.g., adhesive, fasteners, etc.) to create an apparatus as described herein. The ophthalmic lens can also include a portion that houses the optical filter, allowing for rotation of the optical filter relative to the main body portion as discussed further herein.

An optical axis 110 can be oriented through the optical filter 104 and the ophthalmic lens and further extend to an eye 116 of a patient. The optical filter 104 can be substantially planar or can have one or more curved surfaces. The optical filter may be constructed from an optically transparent material (such as polymethylmethacrylate, glass, or sapphire) such that light from a light source 114 (e.g., a coherent light beam) can be transmitted through the optical filter 104 toward the eye 116 generally along the optical axis 110 and filtered using, e.g., a non-transmissive material on a portion of one or more of the surfaces of the optically transparent material, before it reaches the retina 118 of the eye 116. In other embodiments, the optical filter can be constructed from a non-transmissive material such as aluminum and holes or similar perforations can be formed through the material to allow light from a light source to be transmitted through the optical filter 104 toward the eye 116.

The light source 114 can be any type of light source that generates power sufficient to deliver the desired therapeutic effect. For example, the light source 114 can be a laser that produces a coherent light beam having a wavelength of about 400 nm to 650 nm, power of about 0.1 J to 2.5 J, and/or can be configured as a constant beam or applied in timed pulses (e.g., about 1 ns to 5 ns). Additionally or alternatively, the light source 114 can be a grid or array of light emitting diodes (LED) focused through the ophthalmic lens 100. Other light generating devices capable of providing the desired power could also be employed. A light source having a wavelength of 532 nm is preferred.

The optical filter 104 may include a distribution pattern that acts as a distributive or filtering element 108 that is configured to filter power from a light source and which creates a pattern that selectively targets cells of a retina 118. After power is distributed from the light source 114, plural light beams may be focused over a desired area of the retina 118 to selectively target portions of the retina 118 with diseased tissue. In response to this treatment, healthy cells are encouraged to and able to migrate into the treated areas, thereby mitigating the effect of AMD on the eye 116.

As an example, before filtering, the light source 114 may provide a laser beam resulting in a 400 micron spot size at the treatment site. However, an optical filter in accordance with the present invention can separate the power of that beam into a plurality of smaller beams with spot sizes of about 40 microns each. In a preferred embodiment, each of the smaller, filtered beams is separated from another filtered beam by a gap of about 30 to 50 microns. When directed toward the retina of a patient, the plural, smaller beams result in a plurality of targeted, treated cells surrounded by untreated cells. Healthy cells located in the proximate, untreated portions of the retina are then enabled to migrate into the treated regions to improve nutrient flow to the treated portions. This migration has a therapeutic effect on the diseased eye, to mitigate or improve the impact of AMD.

In the example of FIG. 3, the optical filter 104 is located in a plane 112 coincident with a real image of the retina 118. As such, the pattern with which light that passes through the optical filter 104 to impinge on the retina 118 of the eye 116 is representative of the pattern or design of the distributive element 108 of the optical filter 104.

The optical filter and/or distributive element of the optical filter preferably lies in a plane substantially parallel to the plane of the of the ophthalmic lens, for example, as generally shown in FIG. 3. In another embodiment, the optical filter and/or the distributive element of the optical filter can lie in a plane that is offset or angled from the plane of the ophthalmic lens (e.g., at an angle of about 1 to 10 degrees). This type of tilting reduces unwanted reflections and improves the clinician's observation of the treatment area.

Figure 4A:
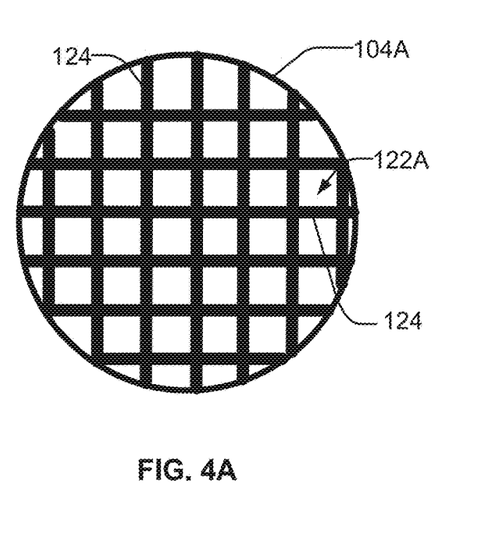
FIGS. 4A-4C illustrate several example filters and distributive elements.
Figure 4B:
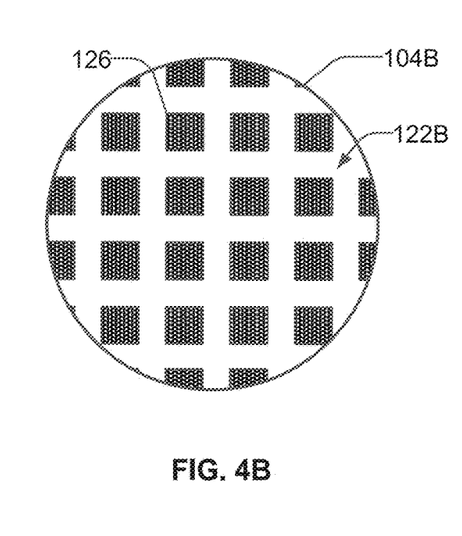
Figure 4C:
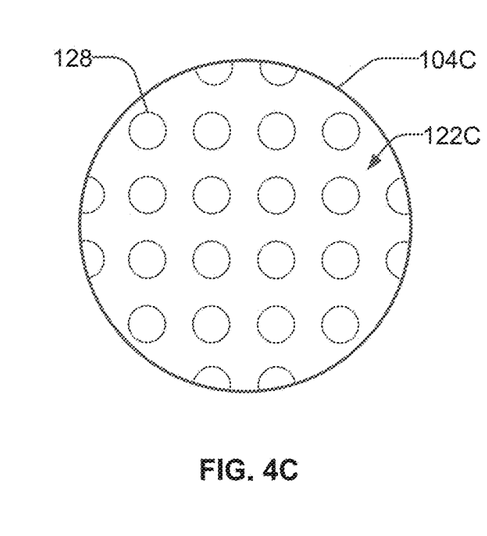

FIGS. 4A, 4B, and 4C illustrate several example distribution patterns for the optical filter 104 disclosed herein.

In the example of FIG. 4A, the optical filter 104A includes a series of generally uniform, intersecting lines or bars 124 on or within an optically transparent material 122A forming an arrangement such as a grid. The lines or bars 124 can be formed on a surface of the material 122A, such as by printing (e.g., 3D printing), deposition (e.g., chemical or vacuum deposition, etc.) and/or etching (e.g., chemical etch, laser and/or mechanical etching, etc.) and are non-transmissive (or non-reflective) such that they generally block power from the beam from passing through the optical filter. In one preferred arrangement, the lines or bars are arranged such that the optical filter creates a plurality of light beams having diameters of about 30 to 50 microns and separated by a space of about 30 to 50 microns. The light beam passes through the optically transparent material 122A while being unable to pass through the lines or bars 123, creating a plurality of light beams for use in treating the retina. The appearance of such a preferred arrangement is a series of squares.

In the example of FIG. 4B, a pattern of reflective squares 126 can be placed on a surface of the material 122B (which may be formed of an optically transparent material), as shown in FIG. 4B. The reflective squares 126 can be formed in a method similar to the lines or bars 124 and described herein. In this example, light impinging on the reflective squares 126 will be blocked in a pattern representative of the transparent portions, or gaps, between the arranged reflective squares 126. Light will therefore pass through gaps between the reflective squares 126, distributing the power of the input light beam. In a preferred embodiment, the reflective squares 126 have a size such that individual RPE cells can be targeted. For example, the squares may be configured such that they would result in a treatment size of about 30 to 50 microns with a gap of about 30 to 50 microns between each treatment site.

In an alternative embodiment, a pattern of non-reflective squares 126 can be formed on a surface of an optically transparent material 1228. In this embodiment, a reflective coating is deposited on a surface of an optical filter (for example as shown at 1228) to create a grid but leaving transmissive or non-coated squares such as squares 126 having a width and height of about 40 microns. The coating thus covers the gap area and there is a gap of about 35 to 40 microns, preferably about 35 microns, between each of the transmissive squares. In this embodiment, light is transmitted through the squares creating a plurality of light beams.

In the example of FIG. 4C, a series of circles or holes 128 can be formed through non-transmissive material 122C (e.g., aluminum) of the optical filter 104C, such as by a molding technique, a laser, mechanical drilling, etc. The size of the holes 128, as well as the spacing between such holes 128, can be selected to impact the eye 116 according to the desired treatment. In another examples, non-transmissive material may be placed over optically transparent material (e.g., glass or PMMA) such that remaining circles or holes of transparent area remain, allowing light to pass through the filter. The circles or holes 128 may be placed at a distance of approximately 30 to 50 microns on the optical filter allowing for a spot size of 30 to 50 microns at the retina.

It is noted that the distributive pattern used with any particular ophthalmic lens needs to account for any magnification of the beam by the ophthalmic lens. For example, if the lens provides magnification of the beam, the spacing and size of the grid pattern, holes, etc. would need to be adjusted. For example, for a contact lens that generates a real image of the retina with no magnification, the distributive pattern would have features allowing for spacing between reflective and non-reflective (or non-transmissive) portions of the filter of about 30 to 50 microns, which allows for targeted therapy. As another example, for a contact lens with image magnification of 0.5×, the distributive pattern would have to be adjusted and the spacing and square or hole size would be reduced by half (e.g., about 15 to 25 microns, preferably about 20 microns) such that the resulting spot size on the retina would be about 30 to 50 microns with appropriate spacing. As another example, for a contact lens with image magnification of 0.7×, the distribution pattern would have to likewise be adjusted (e.g., about to 21 to 35 microns, preferably about 28 microns).

The distributive or filtering element of the optical filter (for example, 104A, 104B, and 104C) can be constructed from a multiple layer thin film coating which selectively reflects a particular wavelength of light and which may be deposited in the filter pattern. In another example, the distributive pattern on the filter may be formed by additive coating(s), vacuum deposition, printing, etc., with the filter pattern integrally formed during the process. The partitioning lines or bars can be optically opaque (i.e., non-transmissive), thereby selectively distributing energy from the light source directed toward the eye (e.g., by reflection, refraction, absorption, etc.). In an alternative example, lines or bars can be made of thin wires, suspended from a frame, which may be used in the absence of or in conjunction with a transparent optical structure (e.g., optical filter 104). As a result, a pattern of light energy will impact the eye 116 in a pattern representative of the arrangement of the filter pattern (e.g., by lines 124) on the optical filter 104A, 104B, and 104C.

In one embodiment, the optical filter is coated with a coating material such as a selective reflector that reflects particular wavelengths of light. The coating comprising the selective reflector may be deposited on the optical filter by vacuum deposition. A coating which reflects wavelengths of light between about 520 nm to about 560 nm, more particularly 532 nm+/−15 nm, is preferred. Selective reflectors are known in the art including laser safety goggles, "hot" mirrors and UV filters. Use of a selective reflector in the optical filter is particularly advantageous as it prevents transmission of particular light through the filter including through portions of the filter that are optically transparent. This clarifies or brightens the image for the clinician and allows for improved imaging and optics.

While the filter pattern on the optical element is generally uniform, the filter may have a non-uniform pattern. The filter pattern is preferably placed on a surface of the optical filter that is closest to the light source but it can also be placed on the side closest to the ophthalmic lens or on both sides. In some embodiments, for example, when using holes through a non-transmissive material, the holes may penetrate the entirety of the filter such that the beam can be transmitted through the holes to the retina.

In one embodiment, an optical filter is manufactured using non-transmissive material. For example, a photoresist is placed on a piece of glass (e.g., by printing or silk screening) to form the desired pattern of dots, squares, etc. A multi-layer coating forming a selective reflector is then deposited on the treated glass via known processes such as vacuum deposition. The photoresist is washed off, leaving a pattern of selective reflector (dots, squares or lines for example). The glass is then cut and mounted in appropriate housing.

Figure 5:
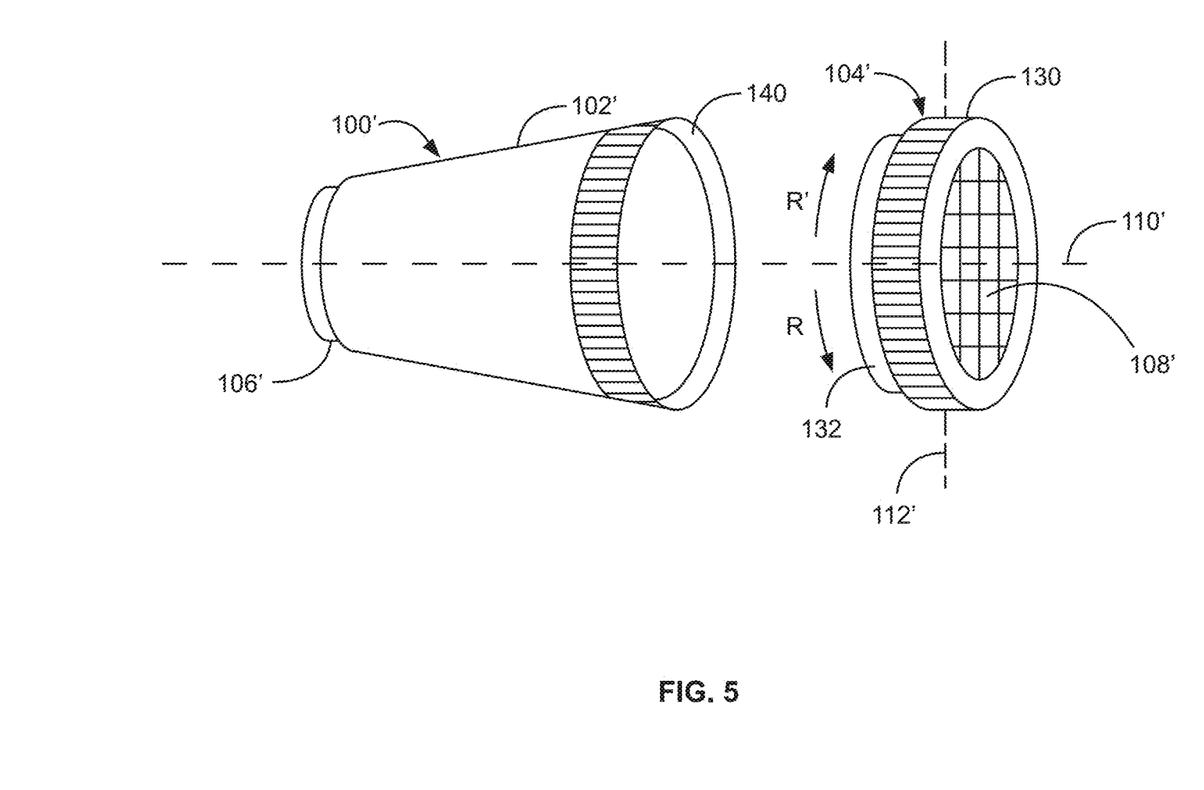
FIG. 5 depicts another example apparatus with an eye contacting lens and optical filter.

FIG. 5 shows another example system including ophthalmic lens 100' and an optical filter 104'. In the example of FIG. 5, reference numbers used are similar to those of FIG. 3 where appropriate, distinguished by an apostrophe.

Referring to FIG. 5, located within or as part of the main body portion 102 of the ophthalmic lens 100 is one or more lenses, for example, a focusing lens. The focusing lens (or lenses) can be any type of optical lens, including gradient index lenses, diffraction gratings, and refractive optics (e.g., aspherical, convex, concave, etc.), for example. The focusing lens can be constructed of a variety of suitable materials, and can be formed by injection molding, machining, additive printing, or other suitable technique. The focusing lens may be configured to generate a real image of the retina and may provide magnification.

As shown in FIG. 5, in some cases, the ophthalmic lens 100' includes a housing and has a lens grip 140 as part of its housing at the proximal end of the ophthalmic lens (the end of the lens closest to the clinician and furthest from the eye contacting portion 106'). A portion of the lens housing projects beyond the lens portion of the ophthalmic lens forming a circular flange or projection 140 around the proximal portion of the ophthalmic lens as shown in FIG. 5.

The optical filter 104' can include a filter grip 130, which may surround, contain, or hold the optical portion or the distributive element 108' of the optical filter. The filter grip 130 may be ring-shaped or other suitable shape and allows the clinician to hold or grip the optical filter. In some examples, the grip 130 can include strips or other materials to improve the ability of the clinician to hold the filter.

In one embodiment where the optical filter is not integral with the ophthalmic lens, the optical filter may further include a generally circular flange or projection 132 protruding from one end of the optical filter and that is configured to be seated in, mated with, mounted on, or otherwise fit into the circular housing of the ophthalmic lens. The circular projection or flange 132 may be integral with the filter grip. The circular flange advantageously allows the optical filter to be mounted conveniently within the housing of the ophthalmic lens providing relatively seamless integration of the filter with the ophthalmic lens.

The ophthalmic lens 100' can be configured to mate with the optical filter 104' in a number of other ways. For example, the interface between the filter and the lens can resemble a male-female type connector with one or both portions having a lip to overlap the other. Additionally or alternatively, a fastener (e.g., a clip, a threaded screw, a compression fitting, etc.) can ensure the mating of the two portions remains secure. In some examples, once mated, the relative orientation is fixed. Preferably, the filter is mated with the lens and oriented such that the filter is coincident with the real image plane of the retina generated by the lens.

A clinician can use the filter grip 130 to support and orient the optical filter (and the ophthalmic lens in some cases) before treatment, for example, to alter the optical axis 110 with regard to the eye 116, or when rotation of the optical filter 104' within the grip 130 is needed.

In the example of FIG. 5, the optical filter 104' can rotate in a plane perpendicular to the optical axis 110' (however any appropriate angle of rotation can be used) by moving or turning the grip 130 (which would in turn rotate the circular flange 132) as shown by R and R'. This allows the clinician to adjust where the plural light beams impact the retina. For instance, as the grip 130 is rotated, the pattern of distributed light beams impinging on the retina of the eye 116 will rotate in kind thus affecting the treatment received by the patient In an example, the optical filter 104' may be oriented perpendicularly to the optical axis 110'. In other examples, the optical filter 104 may be at an angle with respect to the optical axis 110'. As such, rotating or turning the grip 130 may affect the pattern of distributed light beams differently and improving the options for patient treatment if appropriate. It is preferred that during treatment, however, that the ophthalmic lens and optical filter are secured.

Figure 6:
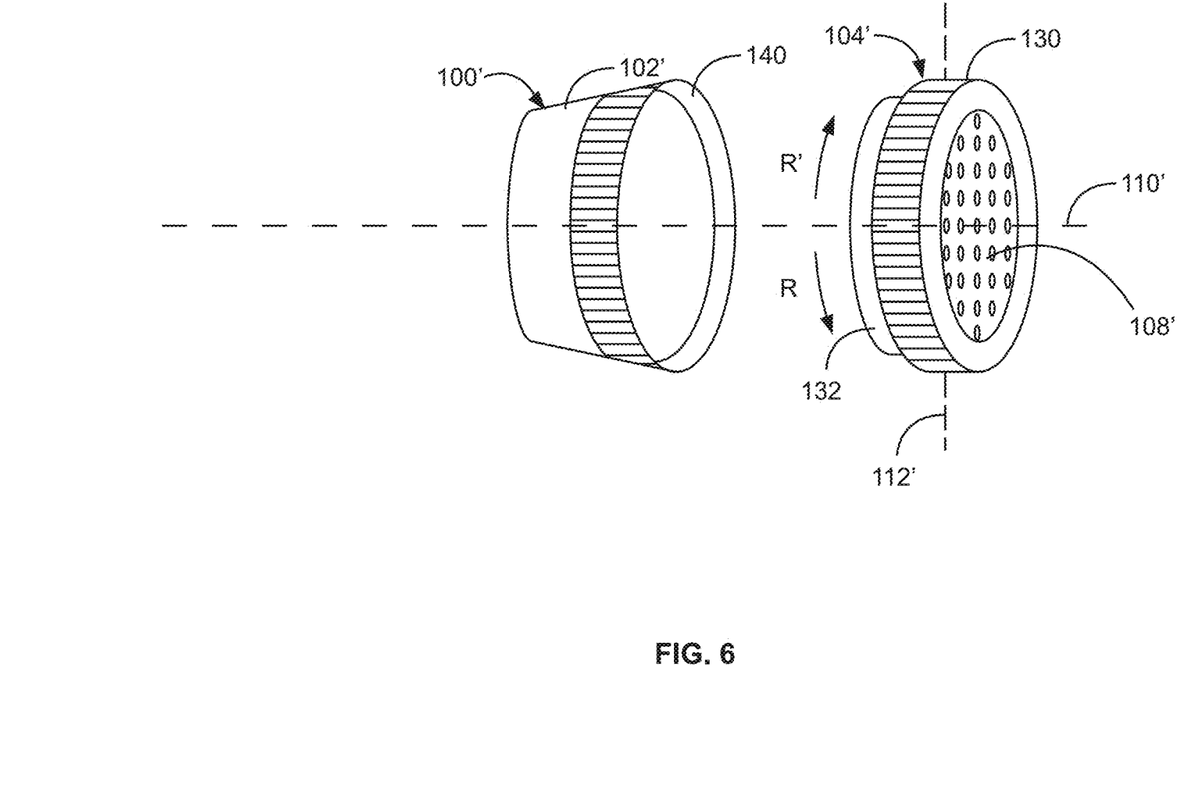
FIG. 6 depicts another example apparatus with an aspheric lens and optical filter.

FIG. 6 shows another example system including ophthalmic lens 100' and an optical filter 104'. In the example shown in FIG. 6, the system has many features similar to the apparatus of FIG. 5; however, an aspheric lens 100' is used and an alternative distributive element 108' with circles or holes is employed.

In the novel method of treating macular degeneration, the apparatus or system described herein is used. The patient is positioned at a laser delivery slit lamp. The clinician obtains the ophthalmic lens to be used in the procedure as well as an optical filter described herein including, for example, one configured to distribute power from a light beam incident on the optical filter to a retina of a patient's eye. The clinician mates the ophthalmic lens and filter, for example, by mounting the optical filter on the housing of the ophthalmic lens and locks the filter and lens in place. The clinician then positions the apparatus (ophthalmic lens and optical filter) on or near the eye. The clinician then directs power from the light beam through the optical filter and ophthalmic lens onto the retina, treating the patient.

A bench experiment deploying an embodiment the ophthalmic lens system disclosed herein is performed. An optically accurate model eye having accurate representation of retinal structures is used as a therapeutic target. The therapy light is implemented with a suitable selective laser trabeculoplasty (SLT) laser, which is normally used for glaucoma SLT treatment.

In this example, an optical filter is manufactured that has a distributive element similar to that shown in FIG. 4B and that is prepared by vacuum depositing reflective aluminum in squares spaced approximately 30 microns apart on a piece of glass. The resulting assembly is mounted into a housing so that it can be mounted onto an contact lens having a total optical power of 60 diopters. After mating the lens and the optical filter, the assembly is placed in the path of the SLT laser.

The SLT laser is focused through the assembly and into the model eye retinal surface. In an example, the light source produces a 400 micron laser spot with energy ranging from 0.2 J to 2.0 J from a laser with a 532 nm wavelength laser, applied over time at a 3 ns pulse. Through the range of laser power, the levels are incremented until a suitable therapy spot is noted on a model retina.

Figure 7:
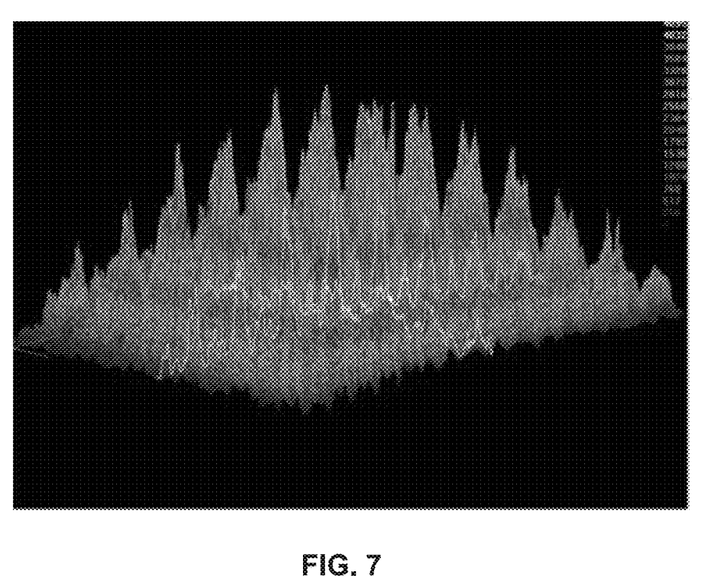
FIG. 7 depicts an elevated side view of distributed light beams delivered to the surface of a model retina.

FIG. 7 depicts the laser energy distribution of the light beams and the resulting therapeutic pattern on the model eye's retinal surface.

The present invention has been described in the terms of the preferred example and it is recognized that equivalents, alternatives, and modifications, aside from those expressly stated, are possible and within the scope of the disclosure.

As utilized herein, the term "exemplary" means serving as a non-limiting example, instance, or illustration. As utilized herein, the terms "e.g.," and "for example" set off lists of one or more non-limiting examples, instances, or illustrations.

While the present method and/or system has been described with reference to certain implementations, it will be understood by those skilled in the art that various changes may be made and equivalents may be substituted without departing from the scope of the present method and/or system. In addition, many modifications may be made to adapt a particular situation or material to the teachings of the present disclosure without departing from its scope. For example, block and/or components of disclosed examples may be combined, divided, re-arranged, and/or otherwise modified. Therefore, the present methods and/or systems are not limited to the particular implementations disclosed, but include all implementations falling within the scope of the appended claims, both literally and under the doctrine of equivalents.

What is claimed is:

1. A handheld apparatus for treating macular degeneration comprising:
   an ophthalmic lens for treatment of macular degeneration in the interior of an eye, wherein the ophthalmic lens comprising a lens housing with a grip portion; and
   an optical filter configured to distribute power from a light beam incident on the optical filter into the ophthalmic lens, the optical filter having:
      a filter housing allowing for the optical filter to be mated with the ophthalmic lens; and
      a surface wherein a portion of the surface comprises non-transmissive material, wherein the non-transmissive material is configured to distribute the power from the light beam into a plurality of light beams directly onto the ophthalmic lens, the plurality of light beams being transmitted through the ophthalmic lens to create a plurality of spots on the retina, and
      wherein a single physical and optical axis extends through each of the ophthalmic lens, the filter housing, and the surface,
      wherein the ophthalmic lens is configured to be releasably mated to the filter housing of the optical filter.

2. The apparatus of claim 1 wherein the optical filter comprises a grid of non-transmissive lines on the surface.

3. An apparatus as recited in claim 2 wherein the optical filter comprises a generally planar structure having first and second surfaces, wherein the first surface is closer to the ophthalmic lens in a mated position than the second surface, and the second surface comprises the grid,
   wherein the physical and optical axis extends substantially through a center of the generally planar structure,
   the optical filter configured to rotate in a plane perpendicular to the physical and optical axis.

4. The apparatus of claim 1 wherein the non-transmissive material on the portion of the surface is configured to create the plurality of spots on the retina having diameters of about 30 to 50 microns.

5. The apparatus of claim 1 wherein the light beam is from a laser applied in a timed pulse from 1 nanosecond to 5 nanoseconds.

6. The apparatus of claim 1 wherein the spacing between two or more spots of the plurality of spots on the retina is about 30 and 50 microns.

7. The apparatus of claim 1 wherein the light beam is from a laser with energy ranging from 0.1 to 2.5 Joules.

8. The apparatus of claim 1 wherein the lens housing is configured to receive the light beam and to allow the interior of the eye to be viewed by a clinician through the surface of the optical filter.

9. The apparatus of claim 1 wherein the optical filter is a first optical filter, the lens housing configured to releasably attach to the first optical filter and a second optical filter.

10. A handheld optical filter for treating macular degeneration comprising:
    a surface comprising non-transmissive material configured to distribute power from a light beam incident on the optical filter into a plurality of light beams and directly onto a handheld ophthalmic lens for treatment of macular degeneration in the interior of an eye; and
    a filter housing comprising a grip wherein the filter housing is configured to be releasably mated with a housing of the ophthalmic lens,
    wherein the filter housing is manually rotatable relative to the housing of the ophthalmic lens, and
    wherein a single physical and optical axis extends through each of the surface, the ophthalmic lens, and the filter housing.

11. The optical filter of claim 10 wherein the non-transmissive material on the surface is configured to create a plurality of spots on the retina having diameters of about 30 to 50 microns when used with the light beam.

12. The optical filter of claim 10 wherein the optical filter comprises a distributive element configured to target retinal pigment epithelial cells in a retina.

13. The optical filter of claim 12 wherein the optical filter comprises a grid, where spacing between parallel lines of the grid at a portion of the optical filter at a minimum distance from a source of the light beam is smaller relative to grid spacing at a maximum distance from the source based on an angle.

14. The optical filter of claim 10 wherein the optical filter comprises a grid with generally uniform lines of the non-transmissive material on the surface of the optical filter.

15. The optical filter of claim 10 wherein the optical filter comprises a distributive element that distributes power from the light beam and creates a plurality of light beams, each of which has a diameter of between about 30 and 50 microns.

16. The optical filter of claim 10 wherein the non-transmissive material is configured to distribute power from a light beam that has a diameter between about 100 and 5000 microns.

17. The optical filter of claim 10 wherein the non-transmissive material is configured to distribute power from a coherent light beam.

18. The optical filter of claim 10 wherein the distributed power from the light beam impinges on the retina of the eye as a plurality of light beams having a diameter between about 30 and 50 microns.

19. The optical filter of claim 10 wherein the optical filter comprises etched lines on the surface of the optical filter.

20. The optical filter of claim 10 wherein the optical filter is a transparent planar structure orientated generally perpendicular relative to the physical and optical axis that extends through the filter housing, the surface, the optical filter and the ophthalmic lens.

21. The optical filter of claim 10 wherein the optical filter is injection molded and/or compression molded and is formed of a material that has an index of refraction between about 1.35 and 1.7.

22. The optical filter of claim 10 wherein the non-transmissive material on the optical filter comprises a selective reflector.

23. The optical filter of claim 22 wherein the selective reflector reflects a wavelength between about 520 to 550 nm.

* * * * *